United States Patent [19]

Hsu

[11] Patent Number: 5,741,709
[45] Date of Patent: Apr. 21, 1998

[54] MULTIPLE INJECTION ANALYSIS

[75] Inventor: Tien-Tsai Hsu, Hsinchu, Taiwan

[73] Assignee: Industrial Technology Research Institute, Hsinchu, Taiwan

[21] Appl. No.: 573,856

[22] Filed: Dec. 18, 1995

Related U.S. Application Data

[63] Continuation-in-part of Ser. No. 220,292, Mar. 30, 1994, abandoned.

[51] Int. Cl.$^6$ .................................................. G01N 35/08
[52] U.S. Cl. ............... 436/52; 436/63; 436/150; 436/174; 436/179; 436/180; 436/807; 422/81; 422/82.01; 422/82.02; 422/82.12; 73/864.21; 73/863.71
[58] Field of Search ................... 422/81, 82, 82.01, 422/82.02, 82.12; 436/43, 52, 63, 150, 151, 174, 179, 180, 806, 807; 73/864.21, 864.91, 863.71

[56] References Cited

U.S. PATENT DOCUMENTS

| | | | |
|---|---|---|---|
| Re. 32,920 | 5/1989 | Matson et al. | 422/82.01 |
| 3,298,934 | 1/1967 | Angeleri | 422/820.01 |
| 4,108,602 | 8/1978 | Hanson et al. | 436/52 |
| 4,319,884 | 3/1982 | Wilson et al. | 422/68 |
| 4,328,185 | 5/1982 | Reasons et al. | 422/82 |
| 4,610,170 | 9/1986 | Ekholm et al. | 73/864.22 |
| 4,740,356 | 4/1988 | Huber | 422/81 |
| 4,865,992 | 9/1989 | Hach et al. | 436/51 |
| 4,873,057 | 10/1989 | Robertson et al. | 422/75 |
| 4,888,998 | 12/1989 | Buzza et al. | 73/864.22 |
| 4,987,785 | 1/1991 | Spencer | 73/863.71 |
| 5,045,284 | 9/1991 | Smith et al. | 422/81 |
| 5,047,212 | 9/1991 | Blades et al. | 436/146 |

*Primary Examiner*—Long V. Le
*Attorney, Agent, or Firm*—W. Wayne Liauh

[57] ABSTRACT

An apparatus for flow injection analysis is disclosed which comprises: (a) an open flow cell containing an upper cell body, a lower cell body contiguously affixed to the upper cell body, and a cell chamber provided in the upper cell body, the cell chamber having a bottom and a top, wherein the top of the cell chamber is open to an atmosphere; (b) a carrier fluid inlet port provided in a lower portion of the upper cell body and in communication with the cell chamber; (c) a fluid delivery device for introducing a carrier fluid into the cell chamber through the carrier fluid inlet; (d) an over-flow outlet setup in an upper portion of the upper cell body to allow exit of the carrier fluid and thus maintaining a constant fluid volume in the cell chamber; (e) a detector disposed in the lower cell body in such a manner that its detecting surface is placed at the bottom of the cell chamber and and facing upward; and (f) a sample injecting assembly, separated from the inlet port and the fluid delivery device for injecting a sample to be analyzed directly onto the detecting surface of the detector without requiring the carrier fluid to carry the sample to the cell chamber. The flow injection analysis disclosed in the present invention combines the advantages of both FIA (continuous operation) and BIA (no dilution by carrier solvent), while eliminating the disadvantages thereof.

13 Claims, 9 Drawing Sheets

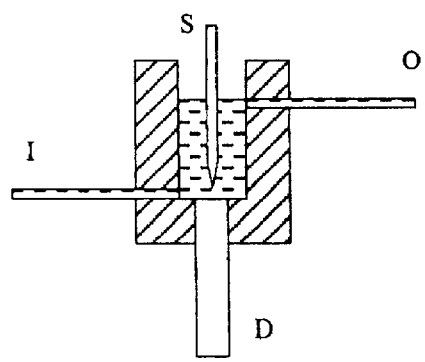
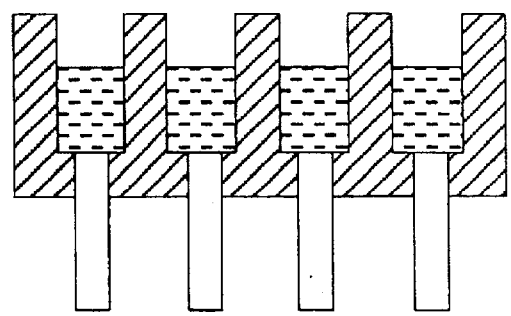
Fig. 4a          Fig. 4b
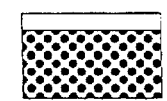
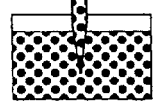
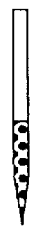
(1)      (2)      (3)
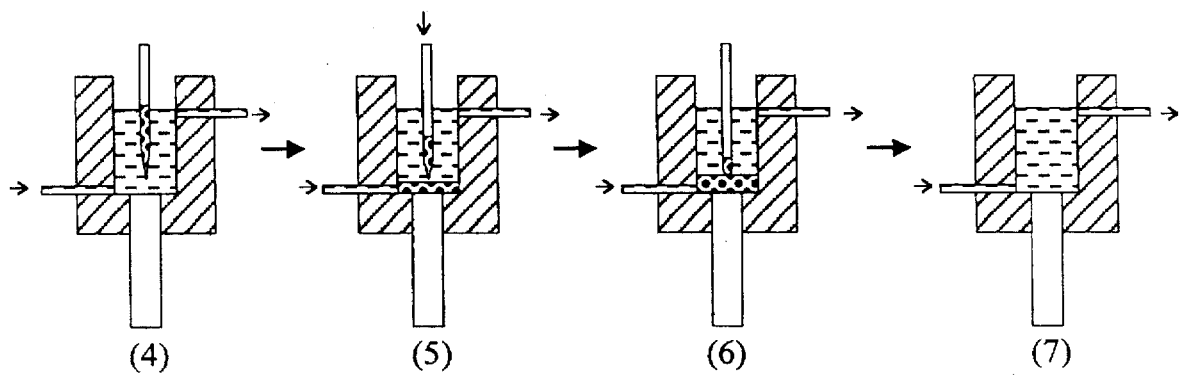
(4)    (5)    (6)    (7)
Fig. 5

MULTIPLE INJECTION ANALYSIS

FIELD OF THE INVENTION

This is a continuation-in-part application of application Ser. No. 08/220,292, filed Mar. 30, 1994, now abandoned. This invention relates to an apparatus for performing clinical analysis which provides high resolution, requires a small sample volume, and is conducted on a continuous basis.

BACKGROUND OF THE INVENTION

Laboratory tests are very important in medical care. Test results help the clinician not only during prognosis and diagnosis but also during the course of treatment. The high demand for clinical analyses in medical care have led to the development of a large number of new analytical technologies and instruments.

Before the AutoAnalyzer (made by Technicon Instruments Co.) was introduced by Skeggs into clinical laboratories in 1957, most of the clinical samples were tested by the manual methods. Due to its mechanical simplicity and flexibility to perform traditional analyses, the AutoAnalyzer had been widely used in centralized clinical laboratories for more than two decades. The development of computers, chemometrics, transducers, enzymatic analysis, immunodiagnostics, and many other technologies has made the success of the Skeggs automated analyzer now legendary. Multichannel instruments have been developed and miniaturized allowing the volumes of both the sample and reagent to be minimized. Examples include the new generation of Technicon AutoAnalyzers, the SMAC, which is based on the analytical principles very similar to the old analyzer described by Skeggs. In general, nowadays the instruments used in centralized clinical laboratories are highly automated. They are characterized by high sample throughput, accuracy and reproducibility.

Because of the high expense and the need for skilled personnel, those instruments are not acceptable for all clinical laboratories. Clinical laboratories that fall into this category include physicians office laboratories, independent laboratories, and nursing houses, which are characterized as being decentralized and having small capacity. Because the quantity of samples in decentralized laboratories is usually small, and, consequently the capital investment for the expensive automated instrument cannot be justified.

However, because of the difficulty of the specimen transportation, the need for fast testing results in the critical situation, and the desired accessibility for decentralized laboratories, there is a market push to improve the instrumentation and technologies that can be used by the decentralized clinical laboratories.

Biosensor, flow injection analysis (FIA), and batch injection analysis (BIA) due to their relative low cost and simplify of operation have dragged recently more attention. In this investigation, based on biosensor, FIA and BIA techniques, a novel multiple injection analysis (MIA) system has been developed. The system is named MIA because of its capability of performing multiple component (in parallel) analyses with a simple instrument set up and the analyses is performed in a similar way to those of FIA and BIA.

The first description of a biosensor was given by Clark and Lyons. A biosensor is generally defined as an analytical device incorporating a biological sensing element, which translates the chemical parameters of a system into an optical or electrical signal. A schematic functional block diagram for the description of the biosensors is shown in FIG. 1. Due to the inherent specificity, portability, speed and size advantages, low cost and on-line capability, biosensors are rapidly growing from research laboratories to the clinical environment, especially for the bedside testing and monitoring, home care, self-screening, and in critical care units.

FIA is based on the injection of a liquid sample into a moving, non segmented continuous carrier stream of a suitable liquid. The injection sample form a zone, which is then transported toward a detector, which continuously records the absorbance, electrode potential, or other physical parameter as it continuously changes as a result of the passage of the material through the flow cell. The simplest FIA system consists of a peristaltic pump for propelling a stream of (non segmented) liquid (i.e., a carrier) through a narrow bore tube (typical I.D. 0.5 mm) towards and through a flow through detector as shown in FIG. 2.

Batch injection analysis (BIA) is a new non-flow injection based technique, which was first introduced by Wang and Taha. A BIA system is constructed as shown in FIG. 3. The technique involves the injection of microliter samples into a location not far from the detector, which is immersed in a large volume of stirred solution. The detector records a transient peak-shaped response that reflects the passage of the sample zone over its surface. The magnitude of the peak reflects the concentration of the injected analyte. Such dynamic measurements performed under batch operation yield the result of analytical performance (speed, sensitivity, reproducibility, simplicity, etc.) similar to that observed from the well-established FIA conditions. However, unlike traditional FIA, which employs solution chemistry for homogeneous conversion of the analyte to a detectable species, BIA lacks a solution-handling capability and must rely heavily on active or specific sensing surfaces. Overall, BIA is conceptually similar to FIA, as it is also based on reproducible transport of the sample toward the detector. It is because of the development of BIA is still in an early stage, there are only a limited number of publications. The detectors that have been adapted to BIA systems are amperometric, potentiometric, or a thermistor.

Because of the demands of automated analysis and the attractive features of FIA, FIA has received considerable attention for high-speed analysis of discrete samples. Many of the new techniques have been developed based on the principle of FIA. However with the growing trends toward miniaturisation and the development of active detectors, many groups have recently demonstrated the advantages of placing the detector within the injection valve or on-detector injector. With the on-detector flow cell, samples are repeatedly injected, with a micro syringe, through a rubber septum placed in a nozzle inlet. Such a gas chromatography-like injection is facilitated by the low pressure of FIA systems. The on-detector flow cell is a hybrid of wall-jet/thin-layer injection detector. It has been demonstrated to be a practical device, which addresses the trends toward integration and miniaturisation of FIA system.

A drawback of the on-detector flow cell is that the sample must be injected via a syringe to penetrate the rubber septum. The use of the septum is an obstacle for conducting multiple-analyte parallel analysis, which is important for clinical applications. Therefore, there is a need to develop improved automated analysis systems which eliminate many of the drawbacks of the prior art devices so that they can be conveniently, reliably, and inexpensively used by decentralized laboratories.

SUMMARY OF THE INVENTION

FIG. 4 shows a schematic configuration according to a preferred embodiment of the present invention. The configuration shown in FIG. 4 is a four-channel multiple-injection analyzer (MIA) cell. Of course, the analyzer disclosed in the present invention can consist of only one analyzer cell, or more than four channels. The detector (D) could be any kind of active transducer, and, in this instance, a commercially available glassy carbon electrode was used as the working electrode of the amperometric detection. The carrier inlet (I) is connected to a stainless steel tube and it is used as the counter electrode in three-electrode electrochemical configuration. The reference electrode could be immersed in the flow stream at the inlet or outlet (O) end. The carrier, which flows through the cell, is driven by using a pump or simply by placing the carrier bottle at a position higher than that of the cells and is driven by gravity. The volume of the carrier in the cell is kept constant by using an over-flow system. The over flow of the carrier can be removed by using a pump or a vacuum bottle at the end of out flow tubing. Samples are introduced by using a pipette or syringe, or any other forms of dispensers. The introduction of samples (S) results in transient responses which are corresponded to the analyte concentrations. The measured signal can be recorded using a chart recorder or logged into a computer memory. The test procedure can be operated manually or automatically.

The detailed operational procedure of the MIA as disclosed in the present invention is described in FIG. 5. At the sampling stage (1) sample and the dispenser connected to a sampling tip are prepared. At step (2) the sample is drawn by the dispenser into the tip. At step (3) the sample is ready to be injected onto the cell. At step (4) the sample is moved into the cell. At the step (5) the sample is injected and dispersed. At this step a peak-shaped signal is generated and recorded. At step (6) the injected sample is removed by the flowing stream and the signal returned to its background level. At step (7) the system is ready for the next sample. A typical signal resulting from the described procedure is shown in the FIG. 6. The numbers shown in this figure represent to the steps of the procedure.

The present invention differs from FIA, mainly in that the injected sample is not diluted with the carrier stream, thus the resolution is greatly enhanced. On the other hand, the present invention is greatly advantageous over BIA, in that the present invention utilizes a very small cell volume, thus allowing the clinical analysis be performed on a continuous basis. A typical BIA cell has an ID of about 180 mm and a height of at least 100 mm, thus representing a cell volume of at least 2.5 liters. In the design of a BIA cell, the cell volume should be essentially "infinite" relative to the injection sample size, so as to avoid interference. Under this requirement, it is impossible to design a continuous flow system, because doing so would require an excessive use of carrier solvent. In the present invention, on contrast, the cell dimension (typically with an I.D. of about 3 mm) is very close to the expose area of the detection probe (typically with a diameter of about 2 mm). Thus the present invention combines the advantages of both FIA (continuous operation) and BIA (no dilution by carrier solvent), while eliminating the disadvantages thereof.

The present invention can utilize detectors, which are in direct contact with the solution under scrutiny. Electrodes can be used to drive chemical changes that are detected by another sensor, or electrodes can be used to detect the products of chemical changes brought by other processes. The dose chemical relationship between electrode and the solution allows better analytical systems to be developed and provides challenging quotes in the understanding of figures of merit. The main analytical strength of electrochemical detection is the high sensitivity which can achieved with relative simplicity, high speed, and low cost. Electrochemical sensors are typically of two types: potentiometric and amperometric. In potentiometric sensor, such as pH, $Na^+$, and $K^+$ electrodes, the zero current potential developed at a selective membrane or electrode surface in contact with a sample solution is related to the analyte concentration. With amperometric sensors, the electrode potential is maintained at a constant level sufficient for the oxidation or reduction of the species of interest (or a substance electrochemically coupled to it); the current that flows therethrough is proportional to the analyte concentration. Because the MIA of the present invention operates in an open system, i.e., the cell is exposed to atmosphere, an electrochemical transducer is therefore the best choice. In this investigation, amperometric detectors were used.

The present invention also utilizes the technology of thick film screen printing, which is referred to as the fabrication of complex geometric patterns of insulating, and resistive or conductive layers on a ceramic substrate by means of a procedure similar to that of silk screen printing. It is the preferred generic description for the field of microelectronics in which specially formulated pastes are applied onto a ceramic of insulating substrate in a definite pattern and sequence to produce a set of passive components. The technology is based on the screen printing and firing of various pastes on a ceramic substrate. The paste is made of special material mixed with an organic binder. The screen used for paste printing is a fine mesh screen on which the required complex patterns have been printed by photoresist techniques. The firing procedure is required in order to drive off the organic binder and fuse the remaining paste material into a uniform layer firmly bonded to the substrate. Thick film technique shows various special characteristics such as: ability to select a variety of materials;
easy formation of film, pattern and multilayer structure;
easy integration;
high reproducibility and flexibility,
attainment of high accuracy by trimming.

Due to so many advantageous features, recently thick film technology has been extended to other fields, particularly to the sensor and transducer production. Using the thick film technology a $SnO2$ gas sensing detector has been made. Based on the amperometric method, a platinum electrode and a chemically modified carbon electrode for the glucose determination has been prepared. Based on a conductometric method, a sensor for urea has been developed. In this invention, a platinum electrode was prepared using the thick film technology which was used for the amperometric determination of hydrogen peroxide and was combined with the enzymes for the determination of glucose and lactic acid.

BRIEF DESCRIPTION OF THE DRAWINGS

FIG. 4a is a simplified schematic side view of a four-channel multiple-injection-analyzer (MIA) according to a preferred embodiment of the present invention.

FIG. 4b is a simplified schematic front view of a four-channel multiple-injection-analyzer (MIA) according to a preferred embodiment of the present invention.

FIG. 5 is the schematic block diagram showing the operation of an analyzer according to a preferred embodiment of the present invention.

FIG. 5(1)–5(7) are simplified schematic drawings showing the steps involved in the present invention, in which FIG. 5(1) shows a pipette and a sample container; FIG. 5(2) shows the pipette is inserted into the sample container to retrieve sample; FIG. 5(3) shows the pipette is removed from the sample container; FIG. 5(4) shows that the pipette contain the testing sample is place right above the detector of the analyzer of the present invention; FIG. 5(5) shows that the testing sample is being discharged from the pipette; FIG. 5(6) shows that the sample has been discharged from the pipette; FIG. 5(7) shows that the pipette is removed from the analyzer to complete the operation.

DETAILED DESCRIPTION OF THE PREFERRED EMBODIMENT

Figure 1:
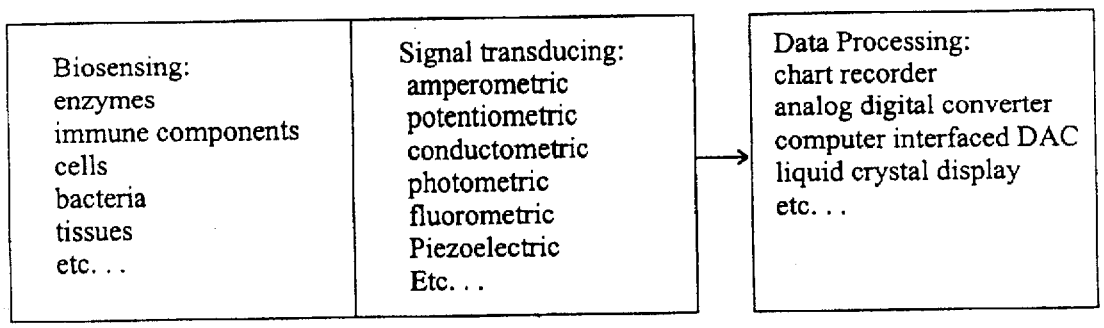
FIG. 1 is a schematic block diagram of a biosensor.
Figure 2:
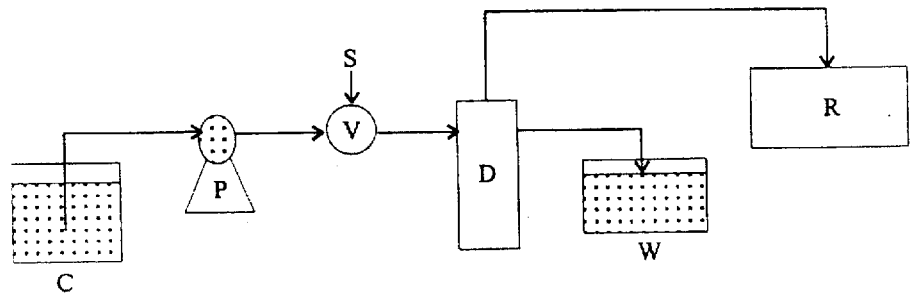
FIG. 2 is a schematic block diagram of the flow injection analyzer (FIA).
Figure 3:
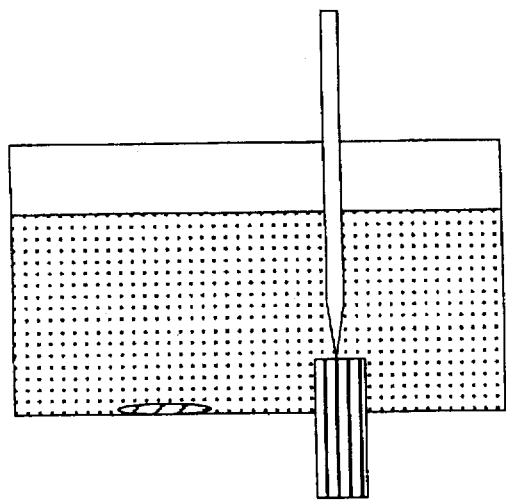
FIG. 3 is a schematic diagram of the batch injection analyzer (BIA).
Figure 6:
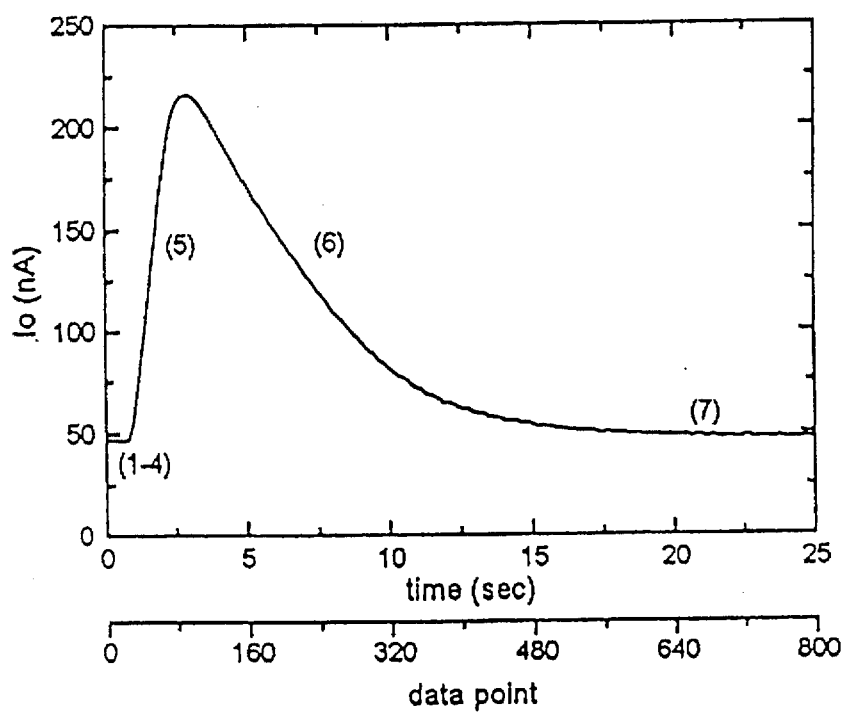
FIG. 6 is a type response curve measured using the analyzer of the present invention.
Figure 7:
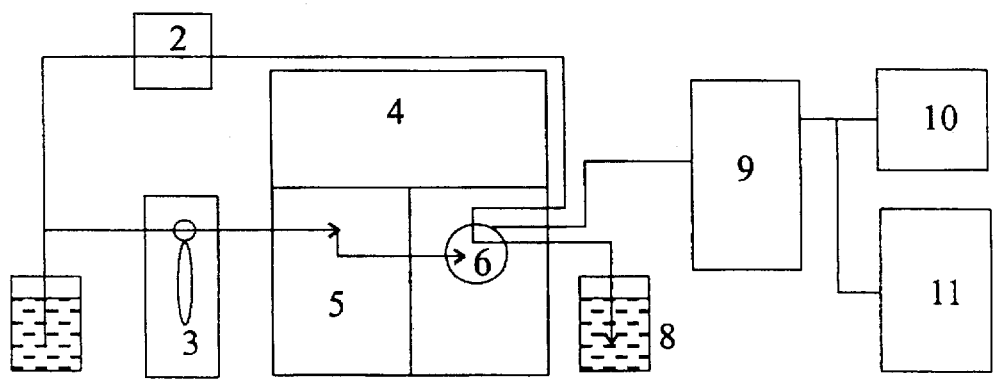
Figure 8:
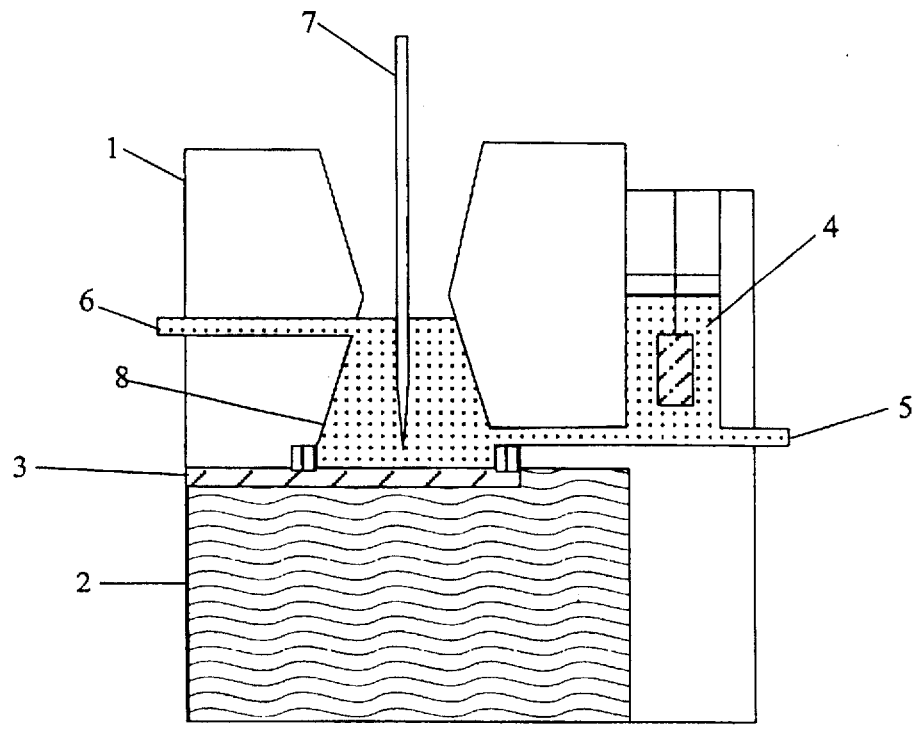
FIG. 8 is a schematic block diagram of an automatic multiple-injection-analyzer cell with a thick film electrode.
Figure 9:
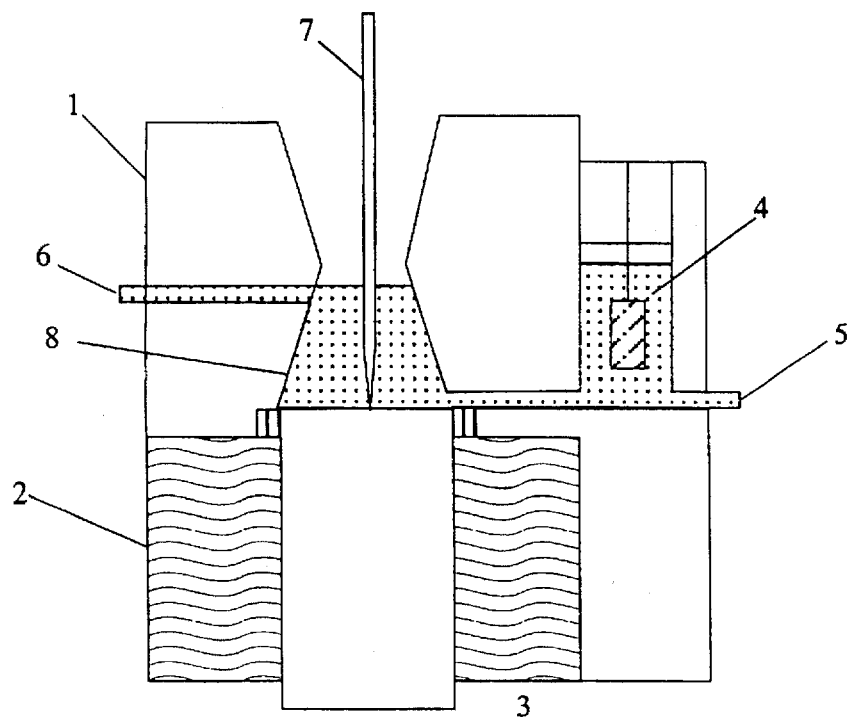
FIG. 9 is a schematic block diagram of an automatic multiple-injection-analyzer cell with a mini-electrode.

FIG. 7 shows the block diagram of an automatic multiple injection analysis system according to a preferred embodiment of the present invention. The carrier solution that flows through the cell was driven by means of gravity or by using a pump. The auto dilutor was equipped in the system to draw the sample and disperse it directly onto the detector. The auto sampler was employed for automatically operation. The solution level was kept constant by means of an overflow method, with a vacuum pump connected at the end of the flow system. Signals were recorded by using a chart recorder and/or a computer. FIG. 8 shows a detailed description of the cell with thick film electrode. The upper 1 and lower 2 parts of the cell body were made of plastic. The printed platinum electrode 3 was used as working electrode and the prepared Ag/AgCl electrode 4 was used as the reference electrode. The carrier inlet 5 and outlet 6 were connected to a stainless steel tube. The inlet stainless steel tube was used also as the counter electrode for a three-electrode electrochemical configuration. The working electrode was fixed by using a O-ring 7. Samples were drawn and injected directly onto the working electrode by using the injection needle connected with to the dilutor.

FIG. 8 shows the MIA cell equipped with a commercial available glassy carbon electrode as the working electrode 3. The rest parts of the cell were the same as the cell described above.

Voltammetric Analysis of Hydrogen Peroxide and Phenol

Voltammetry was used to determine the optimal potential for substance analysis in voltammetry, a variable potential is applied to the working electrode while the current is measured. Cyclic voltammetry involves sweeping the potential between two limits, E1 and E2, at a fixed scan rate. On reaching the potential E2 the scan direction is reversed whilst maintaining the same scan rate. For hydrogen peroxide analysis, 01M potassium phosphate (pH 6.5) with 10 mM KCl was used as carrier solution and for phenol the carrier was 50 mM carbonate buffer (pH 9.6) containing 10 mM KCl.

Immobilization of Glucose Oxidase on AMP-CPG

Glucose oxidase (GOD) (20 mg) was dissolved in 5 ml of 0.01M potassium phosphate (pH 7.0). 100 mg of the glutaraldehyde activated AMP-CPG was then added. The immobilisation was carried out at 4° C. for overnight. The glucose oxidase immobilised CPG was then washed several times with 0.01M potassium phosphate (pH 7.0) to remove the unreacted enzyme. The GOD-COG was then ready for use or stored in buffer at 4° C.

Immobilisation of Lactate Oxidase on AMP-CPG

Lactate oxidase (LOD) (3 mg=100 units) was dissolved in 0.5 ml of 0.1M potassium phosphate (pH 7.0). 50 mg of glutaraldehyde activated AMP-CPG was then added. The immobilisation was carried out at 4° C. for overnight. The immobilised LOD-CPG was then wash with distilled water and 0.1M phosphate buffer (pH 7.0). The immobilised LOD-CPG when not in use was stored in the same buffer at 4° C.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1

Glucose Assay

The reaction involved in the glucose assay is shown as follow:

glucose + oxygen $\xrightarrow{\text{glucose oxidase}}$ gluconic acid + hydrogen peroxide The hydrogen peroxide produced by the GOD catalyzed reaction was then measured amperometrically by using the MIA-GOD (MIA for glucose assay). A commercial available hexokinase method for serum glucose assay kit was used as the reference method.

Materials and Instruments

β-D-glucose and the glucose [HK] kit for quantitative, enzymatic, determination of glucose in serum or plasma at 340 nm were purchased from Sigma (Munich, Germany). The human control serum level 1 (SL1) as normal control and level 2 (SL2) as abnormal control were purchased from Bio-Rad (Bio-Rad Laboratories GmbH, Munich, Germany). The control sera were reconstructed before measurement by adding 5 ml of distilled water and allowing to hydrate by standing still for 15 min at 4° C.

Figure 10:
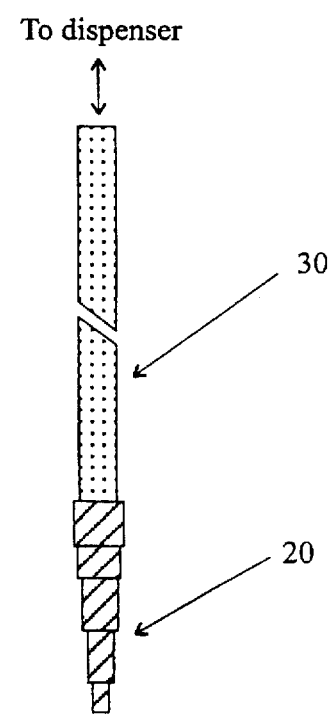
FIG. 10 is a schematic diagram of a packed enzyme reactor connected to a dispenser.

An ELISA reader (Dynatech MR5000, Dynatech Deutschland GrnbH, Germany) was used for the photometric detection. The microliter plate used was purchased from the Nunc Co. (Denmark). The MIA system used for glucose assay was the same as described for hydrogen peroxide determination. The immobilised GOD was packed in a micro-pipette tip as a packed reactor. The reactor 20 was then fixed at the end of the injection needle 30, as shown in FIG. 10.

Optimal Conditions for Glucose Assay

To investigate the influence of pH on MIA-GOD analysis system, the following buffers were used. Citric acid-sodium citrate for the pH range 3.0 to 6.0; potassium phosphatase for the pH range 6.5 to 8.0; Tris-HCl (tris-hydroxymethyl-aminomethane-HCl) for the pH range 8.0 to 10.0; sodium carbonate-bicarbonate for the pH range 9.5 to 10.5. The effect of buffer concentration was studied in concentrations up to 1M. The influence of potassium chloride was investigated from the concentration of 0 to 25 mM. The stock glucose solution was 1M glucose in distilled water. The samples were prepared by diluting the glucose stock solution with different buffers to 1 mM. The sample volume was 75 µl. For the assay the samples were drawn into the immobilised glucose oxidase packed reactor and allowed to react for 5 seconds at room temperature. The hydrogen peroxide produced was then measured by dispersing the reactant into the MIA cell as described above for the hydrogen peroxide determination. The transient respond resulting from the sample injection was recorded with the chart recorder and computer. The experiment was carried out under the control of a computer program.

Glucose Assay Using MIA-GOD

The glucose samples was prepared by dilution with carrier solution. The control sera were reconstructed with 5 ml of distilled water, as indicted in the instruction manual of the product. The reconstructed serum samples were then diluted to appropriate factors with the carrier solution before assay. The procedures of assay were the same as described in the previous paragraphs.

Glucose Assay Using Photometric Method

Photometric determination of glucose was carried out using a commercial kit from Sigma Co. The method was modified from the instruction of the kit (Instruction-Glucose HK, 1991) to use an ELISA reader as detector. The enzymatic reactions involved in the assay are as follow:

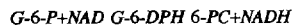

Glucose was first phosphorylated by adenosine triphosphate (ATP), in the reaction catalyzed by hexokinase [HK]. The glucose-6-phosphate [G-6-P] formed was then oxidized to 6-phosphogluconate [6-PG] in the presence of nicotinamide adenine dinucleotide [NAD]. This reaction was catalyzed by glucose-6-phosphate dehydrogenase [G-6-PDH]. During this oxidation, an equimolar amount of NAD is reduced to NADH. The consequent increase in absorbance at 340 nm is directly proportional to glucose concentration. The reagent was reconstructed according to the supplier instruction by adding 20 ml of distilled water. The reconstructed reagent contained approximately the following concentration of active ingredients.

NAD 1.5 mmol/L
ATP 1.0 mmol/L
hexokinase [yeast] 1000 units/L
G-6-PDH [L.m.] 1000 units/L
magnesium ions 2.1 mmol/L
bufferpH 7.5+/−0.1
non reactive stabilizers and fillers
0.05% sodium azide as preservative.

To use the ELISA reader as detector, the sample was first diluted 10 times with the MIA carrier solution. In a microtiter plate 20 µl of the diluted samples were pipettes into each wells. A volume of 180 µl of the reagent was then added (total dilution=100 times ). The reaction was carried out at room temperature for 5 min. The plate was then read by the ELISA reader at wavelength of 340 nm.

EXAMPLE 2 LACTIC ACID ASSAY

The immobilised lactate oxidase (LOD) was used with MIA (MIA-LOD) for lactic acid assay. The reaction of the assay is shown as follow:

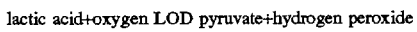

The hydrogen peroxide produced by the LOD catalyzed reaction was detected amperometrically by using MIA-LOD. A commercially available kit for serum lactate assay was employed as the reference method.

Materials and Instruments

L-lactate lithium salt and the lactate kit for quantitative, enzymatic determination of lactic acid in serum or plasma at 540 nm were purchased from Sigma Co. (Munich, Germany). The human control sera and the instruments set up were all the same as described in glucose assay.

Lactic Acid Assay Using MIA-LOD-Single Injection Procedure

For the lactic acid assay, the sample was diluted 50 times with the carrier buffer. A volume of 75 µl of the diluted sample was drawn into the immobilised lactate oxidase packed reactor. The sample was allowed to react for 5 seconds. The reactant was then injected into the MIA cell and the transient response resulted from the sample injection was recorded by using the chart recorder and computer.

Lactic Acid Assay Using MIA-LOD-Two-Step Injection Procedure

Figure 11:
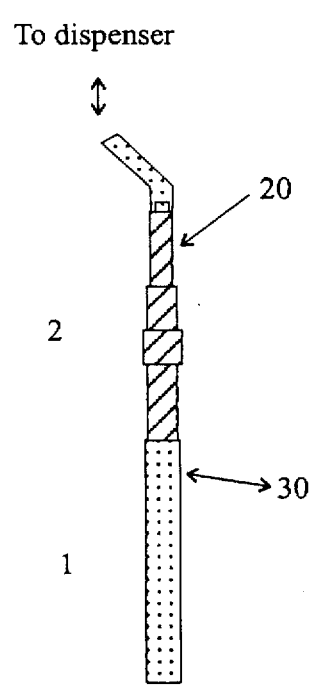
FIG. 11 is a schematic diagram of a two-step injection packed enzyme reactor connected to a dispenser.

The arrangement of the enzyme tip for two-step injection is shown in FIG. 11. The sample preparation was the same as described for single injection procedure. A volume of 80 µl of the diluted sample was drawn into the immobilised lactate oxidase packed reactor. Firstly, a sample volume 21 of 40 µl of the sample which was not contacted with the enzyme was injected. After the first injection the remaining 40 µl of the sample 22, which reacted with the enzyme, was injected. The two injections resulted two peaks which were corresponds to nomenzymatic (background) and enzymatic reaction. By subtracting the signal of enzymatic reaction with non enzymatic signal the net signal of enzyme catalyzed reaction was obtained.

EXAMPLE 3 GLUCOSE ASSAY BY USING MIA (MIA-GOD)

The immobilized glucose oxidase (GOD) was used in MIA for glucose assay. A commercial glucose assay kit for photometric assay of serum glucose was used as the reference method. The optimal conditions of glucose assay using MIA were studied. Control sera were taken as the real serum sample for both methods.

Glucose Oxidase Immobilisation

Glucose oxidase (GOD) was immobilised on two types of aminopropyl control pore glass (AMP-CPG). One was AMP-CPG-550 A, which after the activation with glutaraldehyde showed a pink color. The other was AMP-CPG-1400 A, which showed a light pink color after glutaraldehyde activation. After immobilisation both types of GOD-CPG showed good GOD activity. The type 550 A was chosen for the further experiments because of its larger particle size and because it was easy to handle. The immobilised GOD, when not in use was stored in 0.1M phosphate buffer (pH 7.0) at 4° C. The immobilised GOD had been stored for several months without significant loss of activity. The immobilised GOD also showed high usage stability, one of the packed immobilised GOD tips was used throughout the whole investigation.

Optimal Carrier pH

The pH dependence of the glucose oxidase (E.C. 1.1.3.4, from *Aspergillus niger*) reaction had been investigated in the prior art over a pH range from 3 to 10 at 25° C., with D-glucose as substrate. The optimal pH was 5.5 with a narrow pH range around it. It had also been shown that in an amperometric analysis the pH of the carrier solution affects both enzymatic and electrochemical reactions. In this investigation a broad pH range from 5 to 8 was observed. The optimum was found at pH 6.5 in the presence of a potassium phosphate buffer. Thus the potassium phosphate buffer of pH 6.5 was chosen for the further experiments.

Optimal Buffer Concentration

Figure 12:
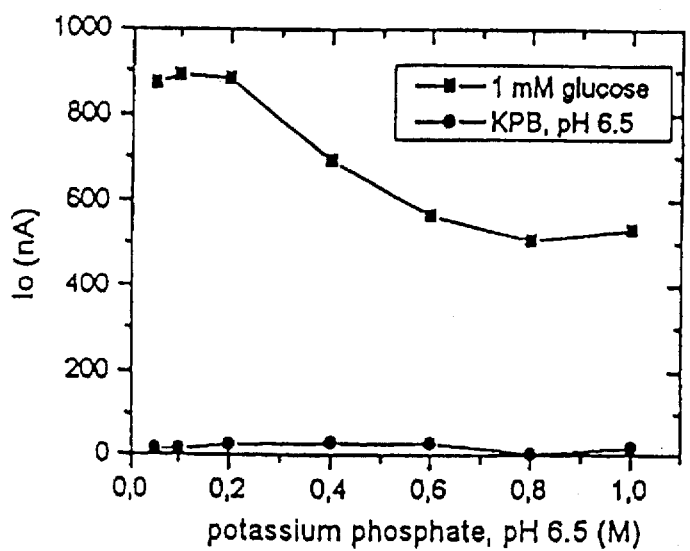
FIG. 12 shows the effect of buffer concentration on MIA-GOD glucose assay.

The products of the glucose oxidation catalyzed by the GOD are gluconic acid and hydrogen peroxide. The gluconic acid produced by the GOD catalyzed reaction can be used to construct the glucose sensor using the potentiometric measurement of pH change. Of the investigated concentrations between 25 mM and 1M, FIG. 12 shows that when the concentration exceeded 200 mM, the magnitude of the measured signal declined. The signal drop at the higher buffer concentration was restored as the buffer concentration was lowered. For the other experiments a buffer concentration of 100 mM was used.

Effect of Potassium Chloride

Figure 13:
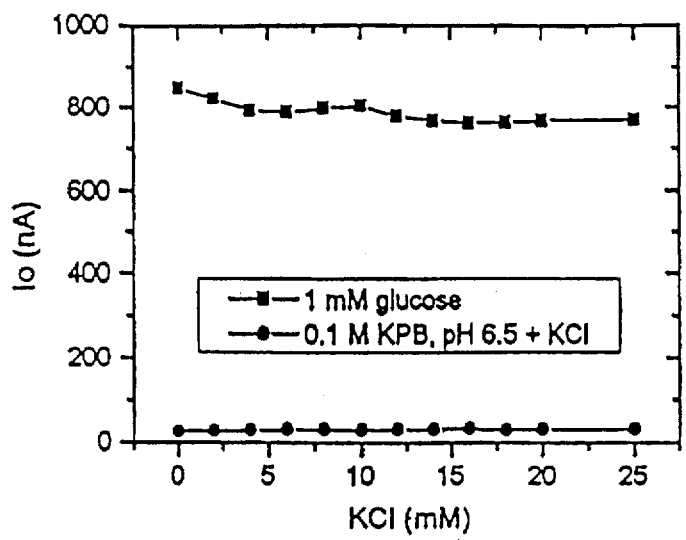
FIG. 13 shows the effect of KCl concentration on MIA-GOD glucose assay.

Potassium chloride is useful as a common electrolyte in the electrochemical analysis, specially when Ag/AgCl electrode is used as the reference electrode. Halide compounds had been proven to be inhibitors of glucose oxidase at lower pH. The effect of potassium chloride on the glucose assay was tested for chloride concentrations from 0 to 25 mM. FIG. 13 shows that the concentration of the potassium chloride had no significant effect on the glucose assay. A 10 mM of potassium chloride was used for the glucose assay using MIA glucose assay.

Dose Response of Glucose Assay Using MIA-GOD

Figure 14:
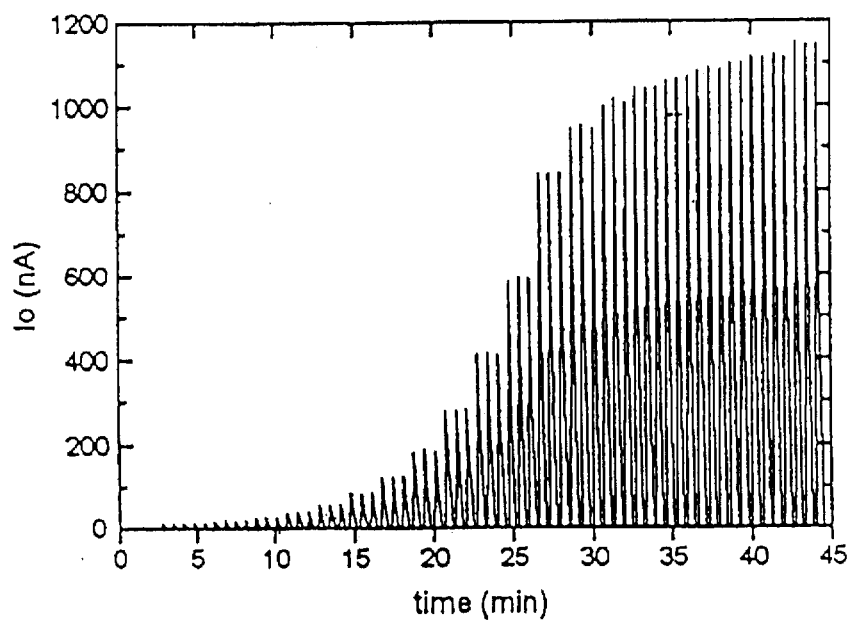
FIG. 14 shows actual signals of a glucose assay using MIA-GOD.
Figure 15:
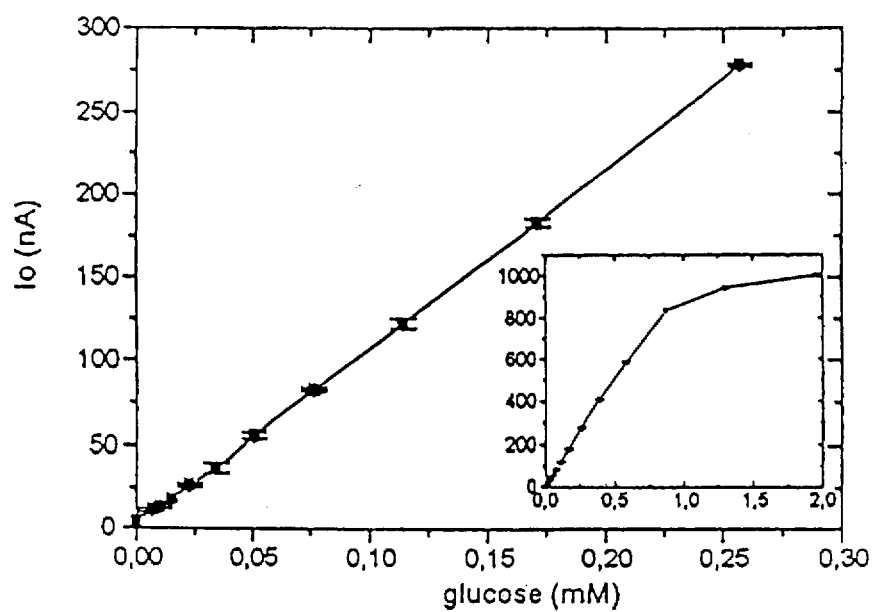
FIG. 15 shows the dose response curve of a glucose assay using MIA-GOD.

FIG. 14 shows a plot of glucose assay measured using MIA. The carrier solution used was 0.1M potassium phosphate buffer (pH 6.5) containing 10 mM KCl. The glucose standard solution was prepared by dilution of glucose stock solution with carrier. FIG. 15 shows the dose response curve of FIG. 14. A linear range was from 0.006 up to 0.75 mM of glucose was observed, by using a sample volume of 75 μl. For concentrations in excess of 0.75 mM the output leveled off. As calculated by using linear regression, the sensitivity of this assay was 1025 nA/mM of glucose. The detection limit based on a S/N ration of 3 was 0.006 rnM (the noise amplitude in the system was 2 nA). The correlation coefficient (R) was 0.999 and standard deviation of mean (SD) was 5.8 nA. The Km value was 0.357 mM. It was determined by repeating the experiments with an oxygenated carrier, that the upper detection limit was due to the oxygen limitation. It was also observed that, by using the oxygenated carrier solution, the background current was higher than that without oxygenated carrier. In case of using oxygenated carrier the detection limit was shifted to a higher concentration but the linear range was the same (data not show). Hence, a carrier without oxygenation was used for the glucose assay. Since glucose concentration in human serum of healthy subjects is in the range from 4.4 to 6.7 mM (80–120 mg/dl) and among abnormal persons, such as diabetic patients, the glucose level may even higher than 30 mM (540 mg/dl), serum samples have to be diluted before assayed by MIA-GOD (MIA glucose assay system).

Dose Response Curve of Serum Glucose Assay Using MIA-GOD

Figure 16:
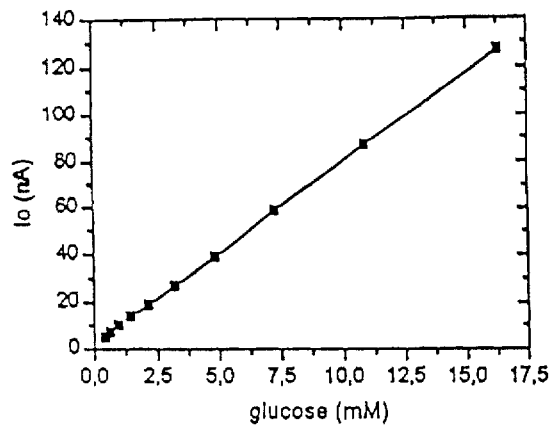
FIG. 16 shows a dose response curve of serum glucose assay using MIA-GOD.

Control serum level 2 (SL2) containing 16.3 mM of glucose was used as a standard for serum glucose assays. As a result of the previous experiments, the samples were diluted 200 times before measurement. The results in FIG. 16 show the dose response curve of the serum glucose measurement. A linear range from 0.424 mM to 16.3 mM was observed. The sensitivity was 7.693 nA/mM (R=0.99987; SD=0.676 mM). If the sensitivity of 7.693 nA/mM is multiplied by 200 (=1538.6 nA/mM) and compared with the result of glucose standard solution (1025 nA/mM), it is found that the slope of the control serum assay was higher than that of glucose standard solution. This distinction may be due to the control serum comprising some electroactive substances such as ascorbic acid which contribute to the output signal. In this investigation a dilution of 50 and 100 times were also tested (data not show) and the results showed an even larger deviation from the result of the glucose standard solution. Therefore, for serum glucose assays the control serum was used as calibrator and a sample dilution of 200 times was used.

EXAMPLE 4 LACTIC ACID ASSAY BY USING MIA (MIA-LOD)

Optimal Buffer pH On MIA-LOD

Figure 17:
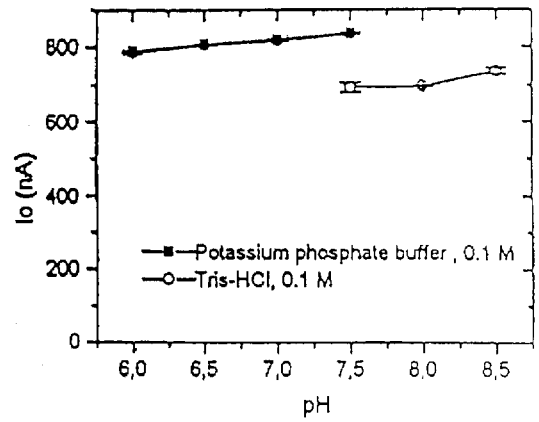
FIG. 17 shows the optimum pH of a lactic acid assay using MIA-LOD.

The effect of the carrier pH on the lactic acid assay by using MIA-LOD was examined from pH 3.0 to pH 10.5. It was found that the activity of the immobilised LOD decreased very fast at pH lower than 6.0 or higher than 8.5. The lost activity could not be rescued as the pH changed to 7.5. While the activity loss was so vast the results using extremely pH value were not reliable. Hence data in FIG. 17 shows only measurements of the pH range between 6.0 and 8.5. In this range, the immobilised LOD showed good activity. The highest signal was found with potassium phosphate buffer, pH 7.5. Thus, this buffer was chosen for the following experiments.

Optimal Buffer Concentration of MIA-LOD

Figure 18:
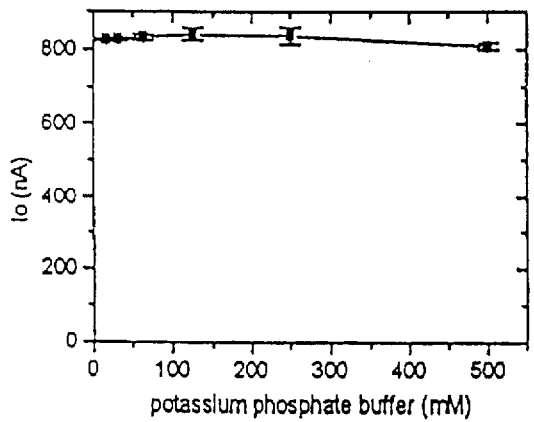
FIG. 18 shows the effect of the buffer capacity on MIA-LOD.

FIG. 18 shows the effect of the buffer capacity on the lactic acid assay. The concentrations were varied from 25 to 500 mM. In this range, the buffer concentration has no significant influence on the signal. The concentration of 0.1M was chosen for the further experiments.

Effect of Potassium Chloride

Figure 19:
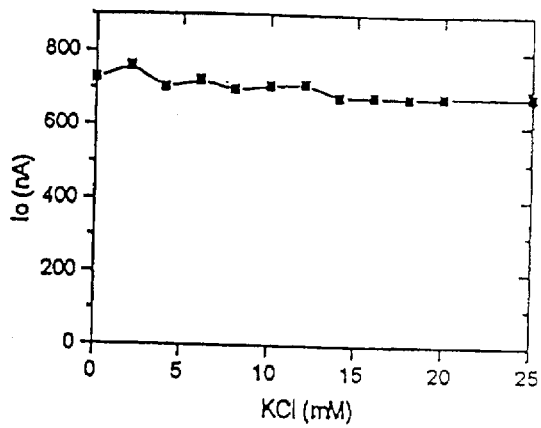
FIG. 19 shows the effect of the KCl concentration on MIA-LOD.

Since potassium chloride had to be added in the carrier, the optimal concentration had to be found. A concentration range from 0 to 25 mM were studied. FIG. 19 shows that within this concentration range no significant influence on the assay was observed. A concentration of 10 mM KCl was chosen for further experiments.

Dose Response of Serum Lactic Acid Assay by Using MIA-LOD

Figure 20:
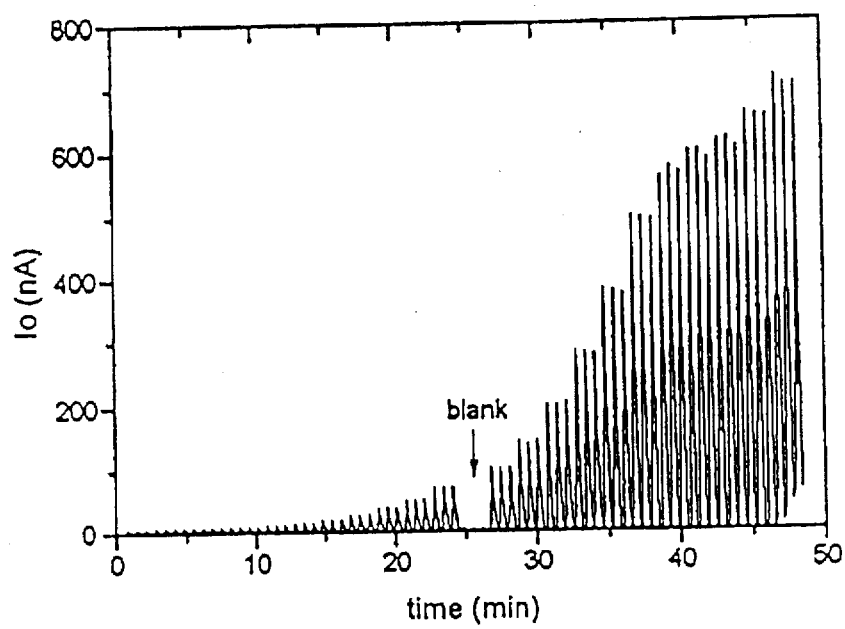
FIG. 20 shows the measured response signals of serum lactic acid using MIA-LOD.

The lactic acid assay was carried out using control serum as the standard solution. The serum standard was prepared by reconstructing SL1 (lactic acid=3.34 mM) with 5 ml of distilled water. Reconstructed SL1 was diluted serially with carrier solution. The diluted samples are then measured by using of a sample volume of 75 µL. FIG. 20 shows the resulting signals.

EXAMPLE 5 SERUM LACTIC ACID ASSAY BY USING TWO-STEP INJECTION

Figure 21:
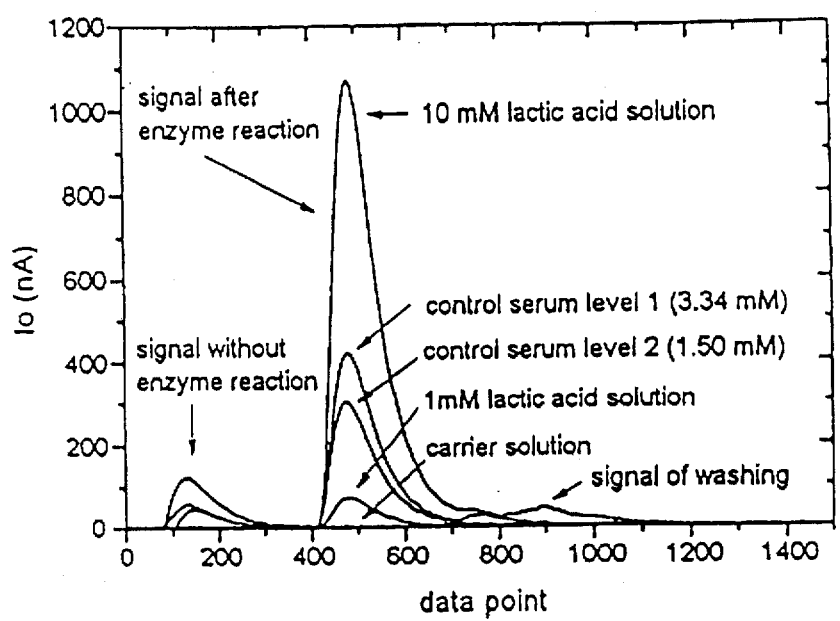
FIG. 21 shows the measured response signals of a two-step injection MIA-LOD.

FIG. 21 shows the measured curves using the two-step injection method. The first peak was related to the first injection. Since the sample zone of the first injection did not react with the enzyme reactor, the signal was regarded as the sample background. The second large peak resulted from the second injection and was related to the sum of the background signal and the signal from the enzyme catalyzed reaction. The third small peak was due to the washing step.

In FIG. 21 SL1 (serum level 1) was regarded as normal control, the lactic acid content is higher than that of SL2 (serum level 2) but the interference level is lower as compared to SL2. The different constitutions of both control sera are clearly detected. The injection of the carrier solution, as blank sample, shows the overall background signal for all the peaks. The injection of sample SL2 resulted in a higher value of the first peak than that of SL1, which was due to the higher interference level of SL2. The larger value of the second peak of the SL1 was related to the higher lactic acid content. In summary the composition of the sample could be detected by two-step injection and background subtraction calculation method. The difference of peak 2 and peak 1 could be used to indicate the net signal resulting from the enzyme catalyzed reaction.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. An apparatus for flow injection analysis comprising:
   (a) an open flow cell containing an upper cell body, a lower cell body contiguously affixed to said upper cell body, and a cell chamber provided in said upper cell body, said cell chamber having a bottom and a top, wherein said top of said cell chamber is open to an atmosphere;
   (b) a carrier fluid inlet provided in a lower portion of said upper cell body and in communication with said cell chamber;
   (c) flow means for introducing a carrier fluid into said cell chamber through said carrier fluid inlet;
   (d) over-flow outlet means in an upper portion of said upper cell body to allow exit of said carrier fluid and thus maintaining a constant fluid volume in said cell chamber;
   (e) a detector disposed in said lower cell body in such a manner that its exposed detecting surface is placed at said bottom of said cell chamber and facing upward; and
   (f) sample injecting means, separated from said carrier fluid inlet and said flow means for injecting a sample to be analyzed directly onto said exposed detecting surface of said detector without requiring said carrier fluid to carry said sample to said cell chamber;
   wherein said cell chamber has a inside-diameter of about 3 mm, and said detecting surface of said detector has a diameter of about 2 mm.

2. The apparatus for flow injection analysis according to claim 1 which further comprises a vacuum to draw said carrier fluid out of said cell chamber when a liquid level of said carrier exceeds said over-flow outlet means.

3. The apparatus for flow injection analysis according to claim 1, wherein said sample injecting means comprises a syringe, a pipette, or an autodispenser, each of which comprises a reaction means selected from the group consisting of chemical reaction and biological reaction means to modify a sample to be tested.

4. The apparatus for flow injection analysis according to claim 1, wherein said detector is a electrochemical sensor, a thermal sensor, or a photo sensor.

5. The apparatus for flow injection analysis according to claim 1, wherein said sample injecting means comprises connecting means for connecting said sample injecting means to an autosampler.

6. The apparatus for flow injection analysis according to claim 1 which comprises a plurality of said open-flow cells and a corresponding number of said inlet means, said flow means, said over-flow outlet means, said detector, and said sample injecting means.

7. A method to perform liquid sample analysis comprising the steps of:
   (a) obtaining an open-flow analysis apparatus comprising:
      (i) an open flow cell containing an upper cell body, a lower cell body contiguously affixed to said upper cell body, and a cell chamber provided in said upper cell body, said cell chamber having a bottom and a top wherein said top is open to an atmosphere;
      (ii) a carrier fluid inlet provided in a lower portion of said upper cell body of and in communication with said cell chamber;
      (iii) flow means for introducing a carrier fluid into said cell chamber through said carrier fluid inlet;
      (iv) over-flow outlet means in an upper portion of said upper cell body to allow exit of said carrier fluid and thus maintaining a constant fluid volume in said cell chamber;
      (v) a detector disposed in said lower cell body in such a manner that its detecting surface is level with said bottom of said cell chamber and and facing upward; and
      (vi) sample injecting means, separated from said carrier fluid inlet and said flow means for injecting a sample to be analyzed directly onto said detector without requiting said carrier fluid to carry said sample to said cell chamber;
   wherein said cell chamber has a inside-diameter of about 3 mm, and said detecting surface of said detector has a diameter of about 2 mm;
   (b) continuously flowing said carrier fluid into said cell chamber through said carrier fluid inlet by said flow means, wherein said volume of said carrier fluid in said open flow cell being kept constant by said over-flow outlet means;
   (c) injecting a sample to be tested directly into said cell chamber and above said detector via said sample injecting means;
   (d) sending output signals transmitted from said detector to a display device or a recording device to as to display or record analysis result;

(e) allowing said sample along with said carrier fluid to exit from said over-flow outlet means; wherein said sample is directly injected into said cell chamber by said sample injecting means without being carried and thus diluted by said carrier fluid to thereby obtain maximum resolution from said detector.

8. The apparatus for flow injection analysis according to claim 1, wherein said sample injecting means comprises a pipette or syringe.

9. A method to perform sample analysis according to claim 7, wherein said open-flow analysis apparatus further comprises a vacuum to draw said carrier fluid out of said cell chamber when a liquid level of said carrier exceeds said over-flow means.

10. A method to perform sample analysis according to claim 7, wherein said sample injecting means comprises a syringe, a pipette, or an autodispersor, each of which comprises a reaction means selected from the group consisting of chemical reaction and biological reaction means so as to modify said sample to be tested.

11. A method to perform sample analysis according to claim 7, wherein said detector is a electrochemical sensor, a thermal sensor, or a photo sensor.

12. A method to perform sample analysis according to claim 7, wherein said sample injecting means comprises a connecting means for connecting said sample injecting means to an autosampler.

13. A method to perform sample analysis according to claim 7 wherein said open-flow analysis apparatus comprises a plurality of said open-flow cells and a corresponding number of said inlet means, said flow means, said over-flow outlet means, said detector, and said sample injecting means.

* * * * *